US012053148B2

(12) United States Patent
Hirota et al.

(10) Patent No.: US 12,053,148 B2
(45) Date of Patent: Aug. 6, 2024

(54) ENDOSCOPE APPARATUS, OPERATING METHOD OF ENDOSCOPE APPARATUS, AND INFORMATION STORAGE MEDIUM

(71) Applicant: OLYMPUS CORPORATION, Tokyo (JP)

(72) Inventors: Masashi Hirota, Hachioji (JP); Jumpei Takahashi, Tokyo (JP); Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 760 days.

(21) Appl. No.: 17/122,810

(22) Filed: Dec. 15, 2020

(65) Prior Publication Data

US 2021/0100439 A1 Apr. 8, 2021

Related U.S. Application Data

(63) Continuation of application No. PCT/JP2018/023316, filed on Jun. 19, 2018.

(51) Int. Cl.
*A61B 1/00* (2006.01)
*A61B 1/06* (2006.01)
*A61B 1/313* (2006.01)

(52) U.S. Cl.
CPC ...... *A61B 1/0005* (2013.01); *A61B 1/000094* (2022.02); *A61B 1/000095* (2022.02);
(Continued)

(58) Field of Classification Search
CPC .......... A61B 1/00009; A61B 1/000094; A61B 1/000095; A61B 1/0005; A61B 1/045; A61B 1/0638; G06T 2207/30101
See application file for complete search history.

(56) References Cited

U.S. PATENT DOCUMENTS 9,943,230 B2   4/2018  Kaku et al.
2009/0180689 A1*  7/2009  Komiya ................. H04N 1/603
                                                    382/167
(Continued)

FOREIGN PATENT DOCUMENTS

JP    2012-125461 A    7/2012
JP    2013-150713 A    8/2013
(Continued)

OTHER PUBLICATIONS

International Search Report dated Sep. 4, 2018 issued in PCT/JP2018/023316, together with an English-language translation.

*Primary Examiner* — John P Leubecker
(74) *Attorney, Agent, or Firm* — Scully, Scott, Murphy & Presser, P.C.

(57) ABSTRACT

An endoscope apparatus includes an illumination device emitting a plurality of lights with different wavelength bands at least two different timings in time series, and a processor including hardware. The plurality of lights includes a first light and a second light. The processor is configured to generate a highlighted image in which a specific structure under a mucus membrane is highlighted, based on a plurality of images obtained by the emission of the plurality of lights. The illumination device emits the first light and the second light continuously. The first light has a first wavelength band corresponding to a luminance component of the highlighted image. The second light has a second wavelength band that enables capturing of an image of the specific structure with higher contrast than the first light.

5 Claims, 9 Drawing Sheets

(52) U.S. Cl.
CPC .......... *A61B 1/0638* (2013.01); *A61B 1/3137* (2013.01); *A61B 1/063* (2013.01)

(56) References Cited

U.S. PATENT DOCUMENTS

| | | | |
|---|---|---|---|
| 2010/0059690 A1* | 3/2010 | Ishihara | A61B 5/489 |
| | | | 250/459.1 |
| 2011/0230715 A1* | 9/2011 | Saito | G06T 7/0012 |
| | | | 600/109 |
| 2012/0130175 A1* | 5/2012 | Koshikawa | A61B 1/0655 |
| | | | 600/178 |
| 2012/0154566 A1 | 6/2012 | Kaku | |
| 2014/0316283 A1* | 10/2014 | Kaku | A61B 5/0084 |
| | | | 600/479 |
| 2016/0331218 A1* | 11/2016 | Kamee | A61B 1/000094 |
| 2017/0236317 A1 | 8/2017 | Yachi | |

FOREIGN PATENT DOCUMENTS

| | | | |
|---|---|---|---|
| JP | 2014-33777 A | | 2/2014 |
| JP | 2014033777 A | * | 2/2014 |
| WO | 2011/125457 A1 | | 10/2011 |
| WO | 2016/067425 A1 | | 5/2016 |

\* cited by examiner

ENDOSCOPE APPARATUS, OPERATING METHOD OF ENDOSCOPE APPARATUS, AND INFORMATION STORAGE MEDIUM

CROSS REFERENCE TO RELATED APPLICATION

This application is a continuation of International Patent Application No. PCT/JP2018/023316, having an international filing date of Jun. 19, 2018, which designated the United States, the entirety of which is incorporated herein by reference.

BACKGROUND

Narrow-band light has different absorption and scattering characteristics depending on its wavelength. A short-wavelength narrow-band image shows microscopic blood vessels in a superficial layer under a mucus membrane and the like. Since these structures are less noticeable in a white light image, an image having the characteristics of both the narrow-band image and the white light image enables more detailed endoscopic observation.

To create an image having the characteristics of both the narrow-band image and the white light image, Japanese Unexamined Patent Application Publication No 2012-125461 teaches capturing an image using white light and an image using narrow-band light, subjecting the narrow-band image to frequency filtering processing, and combining the result of the frequency filtering processing with the white light image.

SUMMARY

In accordance with one of some aspects, there is provided an endoscope apparatus comprising: an illumination device emitting a plurality of lights with different wavelength bands at least two different timings in time series, the plurality of lights comprising a first light and a second light; and a processor including hardware, wherein the processor is configured to generate a highlighted image in which a specific structure under a mucus membrane is highlighted, based on a plurality of images obtained by the emission of the plurality of lights, and wherein the illumination device emits the first light and the second light continuously, the first light having a first wavelength band corresponding to a luminance component of the highlighted image, the second light having a second wavelength band that enables capturing of an image of the specific structure with higher contrast than the first light.

In accordance with one of some aspects, there is provided an operating method of an endoscope apparatus, the method comprising: emitting a plurality of lights with different wavelength bands at least two different timings in time series, the plurality of lights comprising a first light and a second light; and generating a highlighted image in which a specific structure under a mucus membrane is highlighted, based on a plurality of images obtained by the emission of the plurality of lights, wherein the emission of the plurality of lights includes emitting the first light and the second light continuously, the first light having a first wavelength band corresponding to a luminance component of the highlighted image, the second light having a second wavelength band that enables capturing of an image of the specific structure with higher contrast than the first light.

In accordance with one of some aspects, there is provided a non-transitory information storage medium storing a program, the program causing a computer to execute steps comprising: causing an illumination device to emit a plurality of lights with different wavelength bands at least two different timings in time series, the plurality of lights comprising a first light and a second light; and generating a highlighted image in which a specific structure under a mucus membrane is highlighted, based on a plurality of images obtained by the emission of the plurality of lights, wherein the step of emitting the plurality of lights includes emitting the first light and the second light continuously, the first light having a first wavelength band corresponding to a luminance component of the highlighted image, the second light having a second wavelength band that enables capturing of an image of the specific structure with higher contrast than the first light.

DESCRIPTION OF EXEMPLARY EMBODIMENTS

Figure 1:
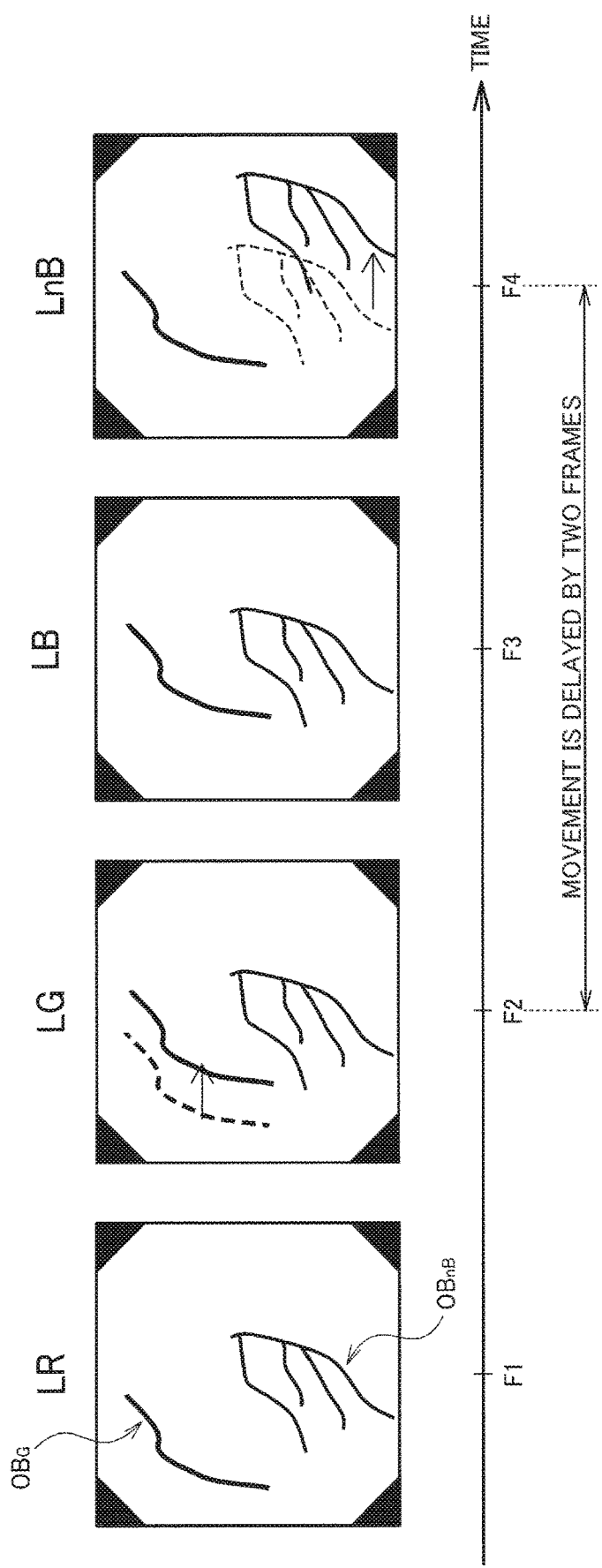
FIG. 1 illustrates the order of emitting illumination lights, and highlighted images, as an example of a comparative example.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. Method in Accordance with the Present Embodiments

In an endoscope apparatus, a frame sequential method of sequentially emitting a plurality of irradiation lights has been widely known. For example, the endoscope apparatus sequentially emits red, green, and blue (RGB) lights corresponding to three primary colors, combines three RGB images sequentially acquired from an image sensor, and thereby outputs a color image. In the following description, a light having an R-band is referred to as a light LR, a light having a G-band is referred to as a light LG, and a light having a B-band is referred to as a light LB. Images captured by emission of the lights LB, LG, and LR are referred to as an LB image, an LG image, and an LR image, respectively.

In the endoscope apparatus, also known is a method of increasing viewability of a predetermined object by emitting a light whose wavelength band is different from those of the lights LR, LG, and LB. For example, a narrow-band light LnB having a partial wavelength band of the B-band is known as enabling capturing of a high-contrast image of a fine vascular structure on a superficial portion of a mucous membrane.

The endoscope apparatus generates a display image by allocating an image to each of a plurality of output channels. The plurality of output channels is, for example, three channels, i.e., a B-channel, a G-channel, and an R-channel. For example, an LB image is allocated to the B-channel of a base image, an LG image is allocated to the G-channel of the base image, and an LR image is allocated to the R-channel of the base image. The base image corresponds to a display image before highlighting processing and is image information composed of the RGB channels.

The endoscope apparatus generates a highlighted image by performing the highlighting processing on the base image, based on an LnB image captured by emission of the narrow-band light LnB. The resulting image can show superficial blood vessels with an increased viewability in comparison with the image before the highlighting processing. In the endoscope apparatus, it is a luminance component that helps a human to recognize a structure or movement of an object easily, and in a more limited sense, it is the G-channel. The highlighting processing on the G-channel of the base image based on the LnB image enables generation of a display image in which the shape and movement of superficial blood vessels are easily recognized. More specifically, information based on the LnB image is added to and combined with the LG image to generate the highlighted image.

However, the conventional technique as disclosed in Japanese Unexamined Patent Application Publication No. 2012-125461 or the like does not consider the order of emitting a plurality of illumination lights in the frame sequential method. Thus, the conventional technique may degrade the quality of a generated display image.

FIG. 1 illustrates the order of emitting illumination lights, and display images, as an example of a comparative example to be compared with the present embodiments. The abscissa axis in FIG. 1 represents time. In the example of FIG. 1, one period corresponds to four frames F1 to F4. The light LR is emitted in the frame F1, the light LG is emitted in the frame F2, the light LB is emitted in the frame F3, and the light LnB is emitted in the frame F4. This cycle is repeated in the subsequent frames, and the lights LR, LG, LB, and LnB are sequentially emitted in each period.

In the frame F1, the LR image is acquired by emission of the light LR. The base image in the R-channel is updated with this acquired image, and thereby the display image is updated. In the endoscope apparatus, as mentioned above, it is the luminance component that helps a human to recognize the structure or movement of the object easily. Thus, the frame F1 shows some change in hue, etc. of the object, but shows a very small movement of the object.

In the frame F2, the LG image is acquired by emission of the light LG. The base image in the G-channel is updated with this acquired image, and thereby the display image is updated. Since the G-channel corresponds to the luminance component, the movement of the object is likely to be reflected in the image. The movement of the object is a relative movement between an insertion section 2 (an imaging optical system 10) illustrated in FIG. 2 and the object. The object in this embodiment is an object $OB_G$ whose image can be captured using the light LG. The object $OB_G$ exemplified in FIG. 1 is a blood vessel having high sensitivity to the light LG.

The light LG is absorbed by hemoglobin less than the light LnB is, and hence has a lower sensitivity to microscopic blood vessels on the superficial portion of the mucous membrane. Thus, the image does not show movement of superficial blood vessels $OB_{nB}$ at a timing of the frame F2. More specifically, the image allocated to the G-channel at the timing of the frame F2 is a highlighted image composed of the LG image that is updated in the frame F2 and subjected to highlighting processing based on the LnB image captured at a past timing. The past timing in this context is an emission timing of the light LnB in the previous period, and indicates a frame preceding the frame F1. That is, since past positions of the superficial blood vessels are maintained, the movement of the superficial blood vessels $OB_{nB}$ in the frame F2 is considered to be small enough.

In the frame F3, the LB image is acquired by emission of the light LB. The base image in the B-channel is updated with this acquired image, and thereby the display image is updated. Thus, similar to the frame F1, the frame F3 shows some change in a hue, etc. of the object, but shows a very small movement of the object $OB_G$.

In the frame F4, the LnB image is acquired by emission of the light LnB. Based on the LnB image, the display image is updated by new highlighting processing on the G-channel of the base image. Since the G-channel corresponds to the luminance component, the movement of the object is likely to be reflected in the image. Specifically, the image shows movement of the superficial blood vessels $OB_{nB}$ extracted from the LnB image.

In the example illustrated in FIG. 1, each period undergoes one movement of the object $OB_G$ whose image can be captured using the light LG and one movement of the superficial blood vessels $OB_{nB}$ as an object whose image can be captured using the light LnB. At this time, the frame F4 which shows the movement of the superficial blood vessels is two frames behind the frame F2 which shows the movement of the object whose image can be captured using the light LG, and this delay degrades image quality. Specifically, when the background area of the image moves, a portion corresponding to the superficial blood vessels fails to follow the movement of the background area, and moves later alone. Such a delayed separate movement gives a feeling of strangeness to a user.

An endoscope apparatus 1 in accordance with the present embodiments prevents degradation of image quality, when generating a highlighted image, by controlling the order of emitting a plurality of illumination lights. The endoscope apparatus 1 in accordance with the present embodiments has a configuration to be described later with reference to, for example, FIG. 2. The endoscope apparatus 1 includes an illumination section 3 and an image processing section 17. The illumination section 3 emits a plurality of lights with different wavelength bands at least two different timings in time series. The image processing section 17 generates a highlighted image in which a specific structure under a mucus membrane is highlighted, based on a plurality of images obtained by the emission of the plurality of lights.

The plurality of lights with the different wavelength bands includes the light LR having a wavelength band corresponding to red, the light LG having a wavelength band corresponding to green, and the light LB having a wavelength band corresponding to blue. Inclusion of the wavelength bands corresponding to the three primary colors enables display of a brighter image having a natural hue to the user. For example, allocation of the LR, LG, and LB images to the R-, G-, and B-channels of the base image, respectively, can provide a white light image as an image before the highlighting processing.

In the present embodiment, various modifications can be made to the plurality of lights with the different wavelength bands. It is possible to omit part or all of the lights LR, LG, and LB, and/or to add a light having a different wavelength band. Various modifications can be also made to the correspondence between the plurality of images acquired by emission of the respective illumination lights and the plurality of output channels. As a modification example, the LG image can be allocated to an output channel different from the G-channel, and a highlighted display image does not exclude an image having a hue different from the white light image, i.e., a pseudocolor image.

The illumination section 3 of the present embodiment continuously emits, out of the plurality of lights, a first light having a first wavelength band corresponding to the luminance component of the highlighted image, and a second light having a second wavelength band that enables capturing of an image of a specific structure with higher contrast than the first light.

The first light is, in a more limited sense, a light for capturing an image allocated to a channel corresponding to the luminance component out of the plurality of output channels. The luminance component represents a channel that has a greater influence on luminance of an output image (the display image and the highlighted image) than the other channels out of the plurality of output channels composing the highlighted image. Specifically, the channel that has a greater influence on the luminance is the G-channel. Taking an R-signal value, a G-signal value, and a B-signal value as R, G, and B, respectively, a luminance value Y can be expressed by $Y = r \times R + g \times G + b \times B$. There are various known methods of conversion between RGB and YCrCb, and values of the coefficients r, g, and b depend on the methods of conversion. In any method, note that g is greater r, and g is also greater than b. Thus, it can be said that the G-signal has a relatively higher contribution to the luminance value Y than the R- and B-signals.

For example, the first light is the light LG, and the first wavelength band ranges from 525 nm to 575 nm. An imaging target of the endoscope apparatus 1 for medical purposes is the inside of a living body. In consideration of the absorption characteristics of hemoglobin contained in blood vessels, the light LG has an important wavelength band for observation of the living body. Allocation of the light LG to the G-channel is advantageous, firstly because the light LG has the wavelength band appropriate for the observation of the inside of the living body, and secondly because the light LG makes the hue of the highlighted image natural. Further in terms of the influence on the luminance of the highlighted image, the light LG gives a greater influence than the light LR allocated to the R-channel and the light LB allocated to the B-channel. In some embodiments, a light different from the light LG may be allocated to the G-channel of the output. In that case, the first light is a light allocated to the G-channel, and the first wavelength band is a wavelength band of this light.

Note that lights have different absorption and scattering characteristics in the inside of the living body depending on wavelengths. For example, in terms of the absorption characteristics, the light LG has lower sensitivity to the microscopic blood vessels. In some cases, depending on absorption characteristics of a substance contained in the object, it may not be easy to differentiate between the specific structure and another structure in the LG image. Thus, the second light having the second wavelength band that enables capturing of the image of the specific structure with higher contrast than the first light is used for observation of such a specific structure.

In this description, "enables capturing of the image of the specific structure with higher contrast" means that an image is captured with a higher viewability of the shape of the specific structure, for example, meaning that a captured image shows edges of the specific structure more clearly than the LG image.

For example, the second light is the light LnB, and the second wavelength band is a wavelength band centering on 410 nm. Note that determination of the second wavelength band depends on a depth at which the specific structure exists, and also on the absorption characteristics of a substance contained in the specific structure. Therefore, a specific wavelength band can be changed variously in accordance with a structure to be focused.

Figure 3:
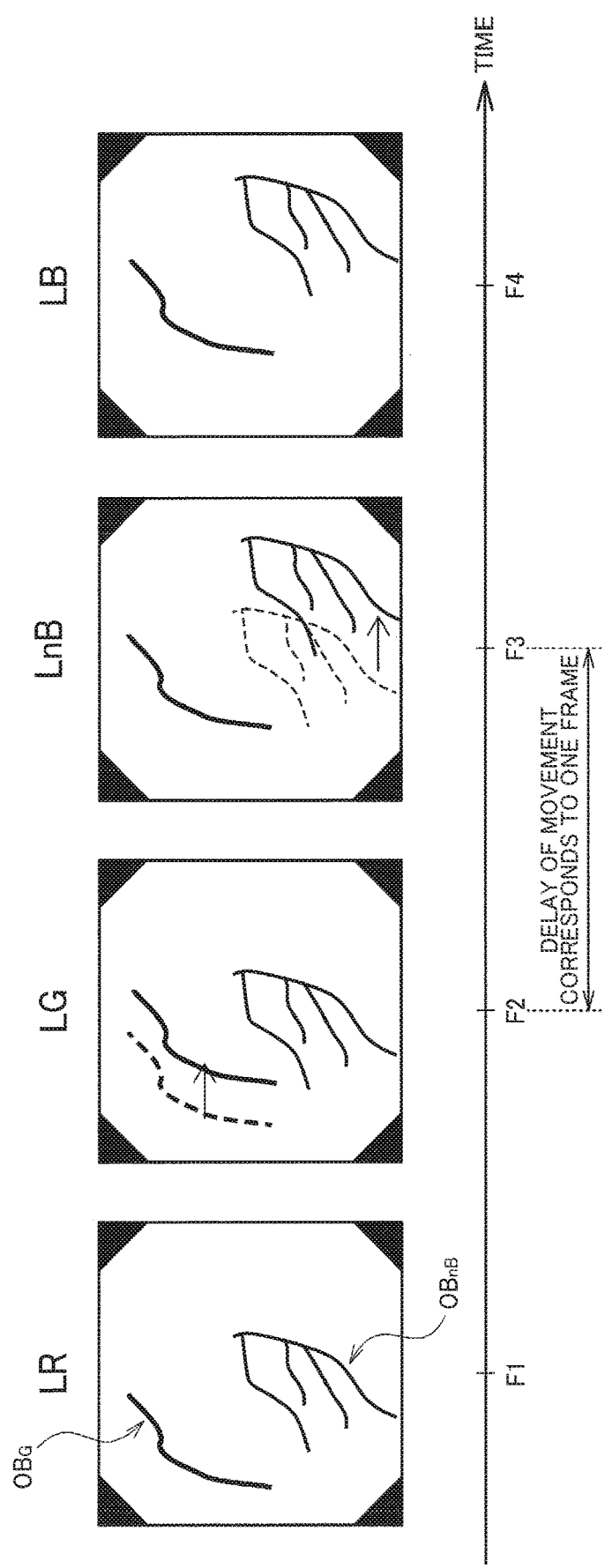
FIG. 3 illustrates the order of emitting illumination lights, and highlighted images, as an example in accordance with a first embodiment.

FIG. 3 illustrates the order of emitting the illumination lights, and highlighted images, as an example in accordance with a first embodiment. In the example in FIG. 3, one period corresponds to four frames F1 to F4. The light LR is emitted in the frame F1, the light LG is emitted in the frame F2, the light LnB is emitted in the frame F3, and the light LB is emitted in the frame F4. This cycle is repeated in the subsequent frames, and the lights LR, LG, LnB, and LB are sequentially emitted in each period.

In the example in FIG. 3, the lights LG and LnB are emitted in consecutive two frames (F2 and F3). Note that the frame in which the light LG is emitted and the frame in which the light LnB is emitted only need to be consecutive, and the two consecutive frames may be the frames F1 and F2 or the frames F3 and F4. Considering the continuity of the periods, it is also possible to emit the light LnB in the frame F1 and to emit the light LG in the frame F4. The order of emitting the other illumination lights, more specifically, the order of emitting the lights LR and LB may be freely selected. Further alternatively, emission of the light LnB may precede emission of the light LG in consecutive frames, as described later in a second embodiment with reference to FIG. 7.

With this configuration, the movement of the specific structure ($OB_{nB}$) whose image is captured using the light LnB is one frame behind the movement of the object ($OB_G$) whose image is captured using the light LG. If the imaging frame rate is 60 fps (frames per second), the time difference is 1/60 second. If the imaging frame rate is 120 fps, the time difference is 1/120 second. In contrast, the delay in the comparative example in FIG. 1 corresponds to two frames. That is, the method according to the present embodiment can reduce the time difference in moving timing of the objects, and can output a highlighted image with a reduced feeling of strangeness to the user.

The specific structure in the present embodiments is, for example, blood vessels. Blood vessels are a useful index of the state of the object (test subject). For example, the number, density, etc. of blood vessels in a captured image are known to vary with the degree of progression of a given lesion. The method in accordance with the present embodiments enables the user to observe even blood vessels which are hard to be observed using the first light, in a highly viewable manner. In a case where the light LnB is used as the second light, the fine vascular structure on the superficial portion of the mucous membrane is highlighted.

The first to third embodiments will be described below. The first embodiment describes details of the method illustrated in FIG. 3. The second and third embodiments describe image processing methods in accordance with the order of emitting the lights LG and LnB.

2. First Embodiment

The first embodiment is now described. First, a configuration of the endoscope apparatus 1 is described with reference to FIG. 2, and thereafter details of processing are described with reference to FIG. 5.

Figure 2:
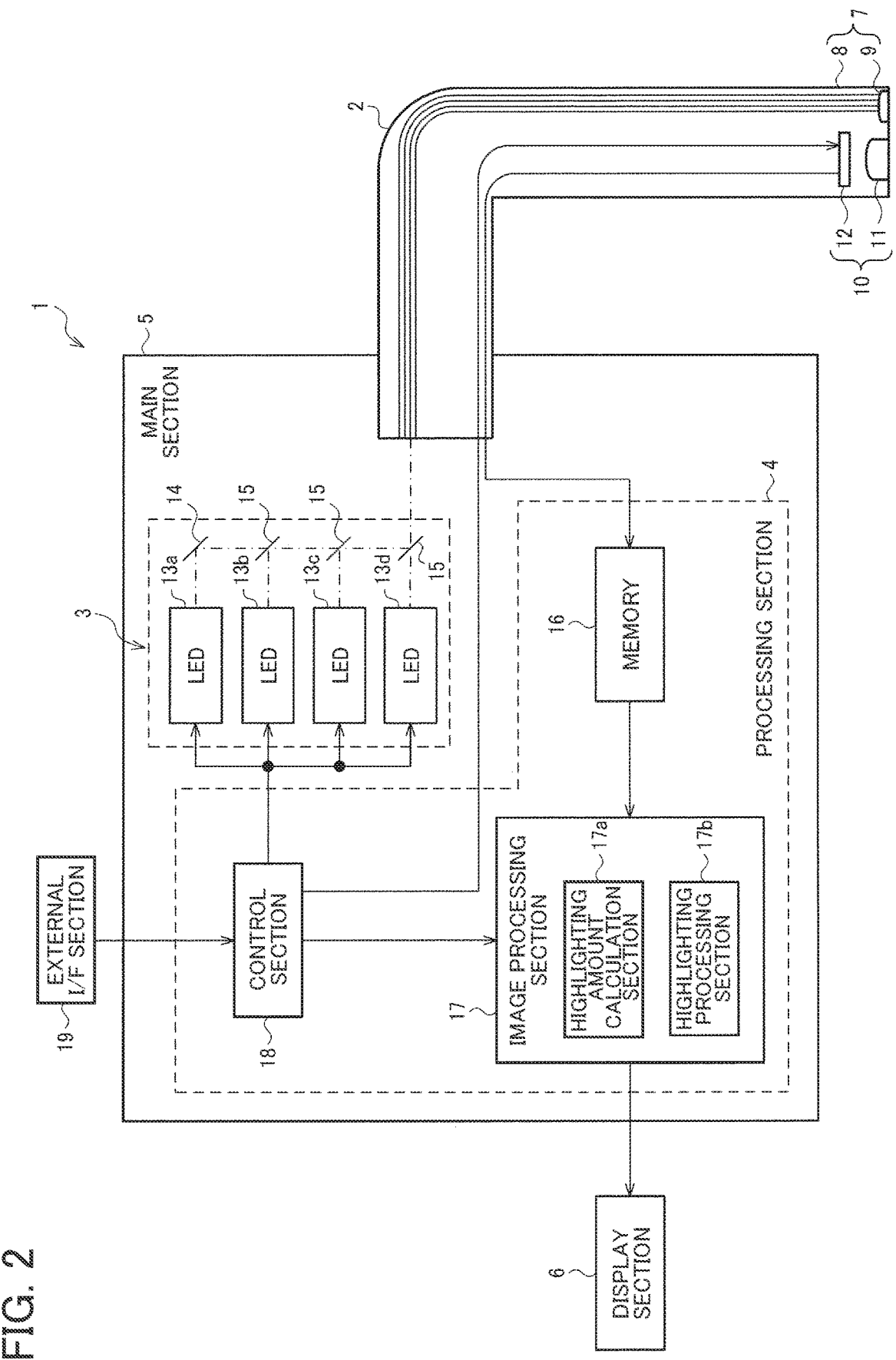
FIG. 2 illustrates a configuration example of an endoscope apparatus.

The configuration of the endoscope apparatus 1 illustrated in FIG. 2 is described in detail. The endoscope apparatus 1 includes an insertion section 2, a main section 5, and a display section 6. The main section 5 includes an illumination section 3 connected to the insertion section 2, and a processing section 4.

The insertion section 2 is a portion to be inserted into the living body. The insertion section 2 includes an illumination optical system 7 that emits light input from the illumination section 3 to the object, and an imaging optical system 10 that captures an image of reflected light from the object.

The illumination optical system 7 includes a light guide cable 8 that guides light entering from the illumination section 3 to a leading end of the insertion section 2, and an illumination lens 9 through which light is diffusively emitted to the object. The imaging optical system 10 includes an objective lens 11 that collects reflected light from the object out of the light emitted by the illumination optical system 7, and an image sensor 12 that captures an image of light collected by the objective lens 11. The image sensor 12 can be implemented by various kinds of sensors such as a charge-coupled device (CCD) sensor and a complementary metal-oxide semiconductor (CMOS) sensor. Analog signals sequentially output from the image sensor 12 are converted to a digital image by an analog/digital (A/D) conversion section, which is not illustrated. Note that the A/D conversion section may be included in the image sensor 12 or in the processing section 4.

The illumination section 3 includes a plurality of light emitting diodes (LEDs) 13a to 13d that emits lights with different wavelength bands, a mirror 14, and dichroic mirrors 15. The respective lights emitted from the plurality of LEDs 13a to 13d are made incident on the identical light guide cable 8 by the mirror 14 and the dichroic mirrors 15. While FIG. 2 illustrates the example of including four LEDs, the number of LEDs is not limited thereto.

Figure 4:
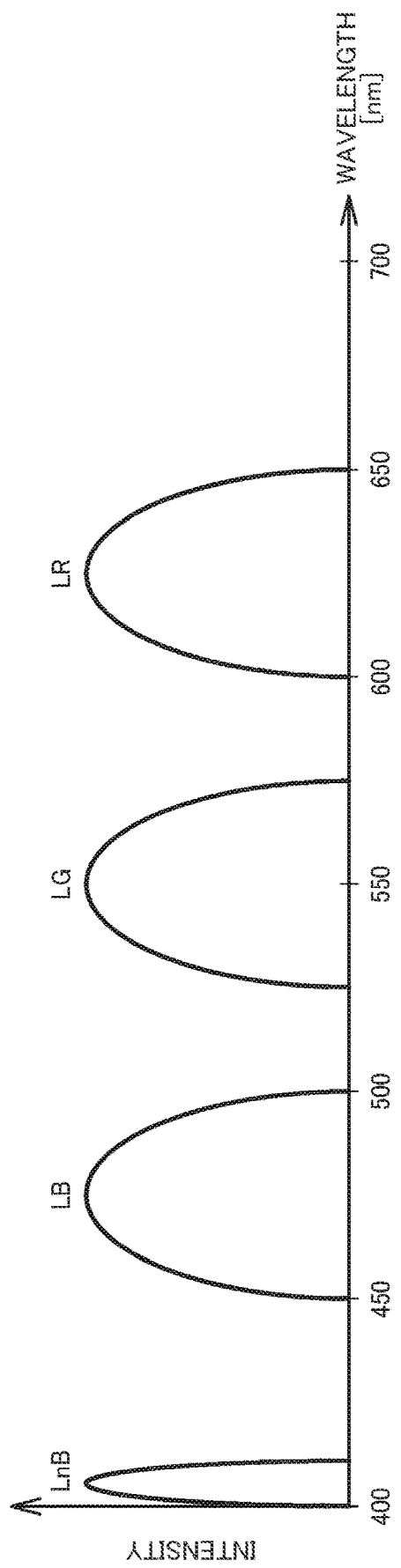
FIG. 4 is a graph indicating an example of spectral characteristics of an illumination section.

FIG. 4 is a graph indicating spectral characteristics of the LEDs 13a to 13d. The illumination section 3 in the present embodiment includes three LEDs that respectively emit the light LB having a blue wavelength band, the light LG having a green wavelength band, and the light LR having a red wavelength band. For example, the blue wavelength band ranges from 450 nm to 500 nm, the green wavelength band ranges from 525 nm to 575 nm, and the red wavelength band ranges from 600 nm to 650 nm. Note that the RGB wavelength bands are not limited thereto, and various modifications can be made. To give an example, the blue wavelength band may range from 400 nm to 500 nm, the green wavelength band may range from 480 nm to 600 nm, and the red wavelength band may range from 580 nm to 700 nm. The illumination section 3 in the present embodiment further includes an LED that emits the light LnB which is a blue narrow-band light. For example, the blue narrow band is a wavelength band centering on 410 nm, and in a more limited sense, a band of about 410 nm±10 nm.

The processing section 4 includes a memory 16, an image processing section 17, and a control section 18. The memory 16 stores an image signal acquired by the image sensor 12 for each wavelength of a corresponding illumination light. The memory 16 is a semiconductor memory such as a static random-access memory (SRAM) or a dynamic random-access memory (DRAM), but may alternatively be a magnetic storage device or an optical storage device.

The image processing section 17 performs various types of image processing on image signals stored in the memory 16. The image processing section 17 includes a highlighting amount calculation section 17a and a highlighting processing section 17b. The highlighting amount calculation section 17a is, for example, a highlighting amount calculation circuit, and in a more limited sense, includes a filter circuit that extracts a predetermined spatial frequency component from an image. The highlighting processing section 17b is, for example, a highlighting processing circuit.

The highlighting amount calculation section 17a calculates a highlighting amount for the highlighting processing, based on the LnB image captured by the emission of the light LnB. The highlighting processing section 17b performs the highlighting processing based on the calculated highlighting amount, and outputs a highlighted image. The highlighting processing as mentioned herein is to increase viewability of a given object in the highlighted image in comparison with the image before the highlighting processing. The highlighted image in the present embodiment is an output image from the processing section 4, and is a display image to be displayed on the display section 6. The image processing section 17 may perform other types of image processing on an image acquired from the image sensor 12. For example, as preprocessing or post-processing of the highlighting processing, the image processing section 17 may perform known processing such as white balance processing and noise reduction processing.

The control section 18 performs control to synchronize an imaging timing of the image sensor 12 and a lighting timing of the LEDs 13a to 13d. The control section 18 is, for example, a control circuit or a controller.

The display section 6 sequentially displays highlighted images output from the image processing section 17. That is, the display section 6 displays a video in which the frame images are the highlighted images. The display section 6 is, for example, a liquid crystal display, an electroluminescence (EL) display, or the like.

An external interface (I/F) section 19 is an interface by which a user performs an input or like operation to the endoscope apparatus 1. That is, the external I/F section 19 is, for example, an interface for operating the endoscope apparatus 1, or an interface for setting operations of the endoscope apparatus 1. For example, the external I/F section 19 includes an adjustment button to adjust a parameter for the image processing.

Note that the endoscope apparatus 1 in accordance with the present embodiment may be configured as described below. That is, the endoscope apparatus 1 (in a more limited sense, the processing section 4) includes a memory that stores information, and a processor that operates based on the information stored in the memory. The information is, for example, a program and various kinds of data. The processor performs image processing including the highlighting processing, and controls emission of light from the illumination section 3. The highlighting processing herein is to determine a highlighting amount based on the LnB image and to highlight the base image based on the highlighting amount.

The processor may implement functions of the respective sections, for example, by individual hardware or by integrated hardware. For example, the processor includes hardware, and the hardware can include at least one of a digital signal processing circuit and an analog signal processing circuit. For example, the processor can be composed of one or more circuit devices mounted on a circuit board, or one or more circuit elements. The circuit device is, for example, an integrated circuit (IC) or the like. The circuit element is, for example, a resistor, a capacitor, or the like. The processor may be, for example, a central processing unit (CPU). Note that the processor is not limited to the CPU, but can be any of various other processors such as a graphics processing unit (GPU) and a digital signal processor (DSP). The processor may be a hardware circuit that includes an application specific integrated circuit (ASIC). The processor may include an amplifier circuit, a filter circuit, or the like for processing an analog signal. The memory may be a semiconductor memory such as an SRAM or a DRAM, or may be a register. The memory may be a magnetic storage device such as a hard disk drive, or may be an optical storage device such as an optical disk device. For example, the memory stores a computer-readable instruction, and the processor executes the instruction to implement a function of each section of the processing section 4 as processing. The instruction may be an instruction set that is included in a program, or may be an instruction that instructs the hardware circuit included in the processor to operate.

Each section of the processing section 4 in the present embodiment may be implemented as a module of a program that operates on the processor. For example, the image processing section 17 is implemented as an image processing module. The control section 18 is implemented as a control module for performing, for example, synchronization control between the emission timing of the illumination light and the image capturing timing of the image sensor 12.

Furthermore, the program implementing the processing performed by each section of the processing section 4 in the present embodiment can be stored, for example, in a computer-readable information storage medium. The information storage medium can be implemented by an optical disk, a memory card, a hard disk drive (HDD), or a semiconductor memory, for example. The semiconductor memory is, for example, a read-only memory (ROM). The processing section 4 performs various kinds of processing for the present embodiment, based on the program stored in the information storage medium. That is, the information storage medium stores the program causing a computer to function as each section of the processing section 4. The computer is a device including an input device, a processing section, a storage section, and an output section. The program causes the computer to execute the processing of each section of the processing section 4.

In other words, the method according to the present embodiment can be implemented as a program that causes a computer to execute steps of causing the illumination section 3 to emit a plurality of lights with different wavelength bands at least two different timings in time series, and generating a highlighted image in which a specific structure under a mucus membrane is highlighted, based on a plurality of images obtained by the emission of the plurality of lights. In the step of emitting the plurality of lights, the program causes the computer to cause the illumination section 3 to continuously emit a first light having a first wavelength band having a great influence on the luminance of the highlighted image, and a second light having a second wavelength band that enables capturing of an image of the specific structure with higher contrast than the first light.

Figure 5:
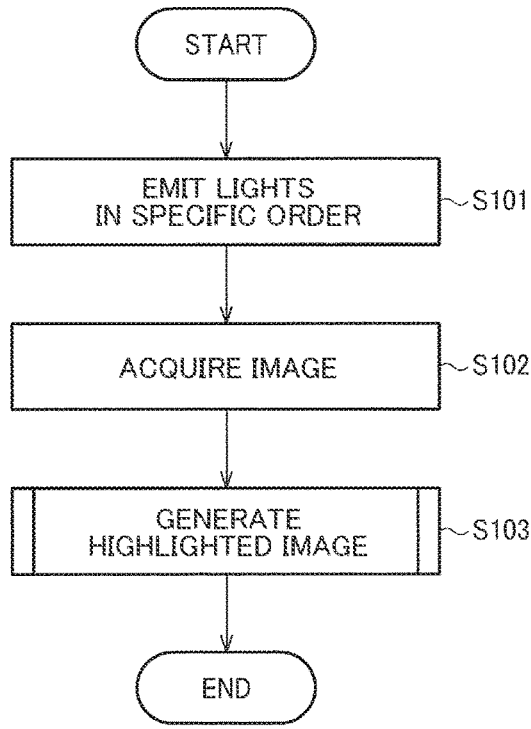
FIG. 5 is a flowchart describing processing by the endoscope apparatus.

FIG. 5 is a flowchart describing processing in accordance with the present embodiment. When this processing starts, the illumination section 3 emits a plurality of lights with different wavelength bands to a living body in a specific order under control of the control section 18 (step S101). The lights with the plurality of wavelength bands in accordance with the present embodiment are, for example, the light LnB having the blue narrow band centering on 410 nm, the light LR having the R-band, the light LG having the G-band, and the light LB having the B-band, which are illustrated in FIG. 4.

The illumination section 3 emits the light LnB immediately after the emission of the light LG as controlled by the control section 18. A specific example of the order of emission is illustrated in FIG. 3. The illumination section 3 emits the lights in the order of "LR, LG, LnB, and LB".

In step S102, the processing section 4 acquires an image based on the emission of each light described in step S101. Processing in step S102 includes A/D conversion processing of output signals from the image sensor 12 and processing of storing the image in the memory 16.

Subsequently, in step S103, the image processing section 17 generates a highlighted image based on each image acquired in step S102. In step S103, the image processing section 17 combines information about the LnB image with the base image composed of the LR, LG, and LB images.

Figure 6:
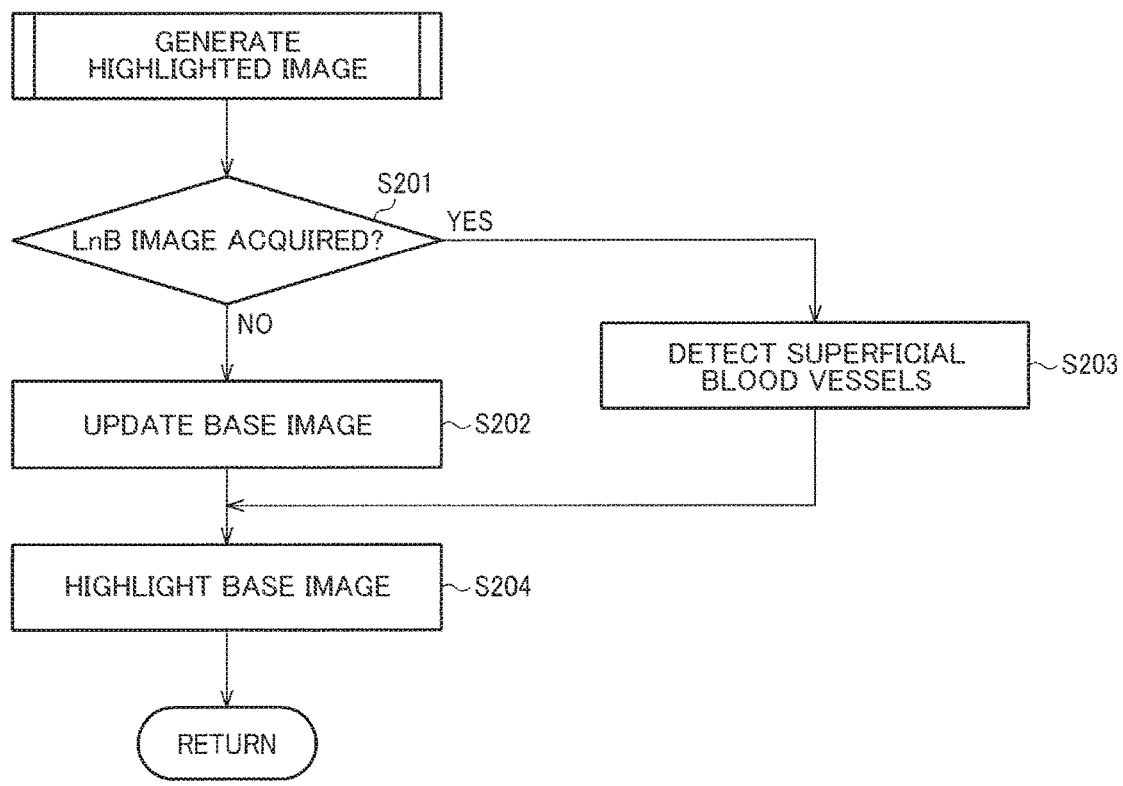
FIG. 6 is a flowchart describing highlighted image generation processing in accordance with the first embodiment.

FIG. 6 is a flowchart describing processing in step S103 of FIG. 5. When this processing starts, the image processing section 17 first determines whether the image acquired in step S102 is an LnB image (step S201). If the acquired image is not an LnB image (NO in step S201), the procedure goes to step S202, where the image processing section 17 updates any one of the channels of the base image. Specifically, if the image acquired in step S102 is an LR image, the image processing section 17 allocates the LR image to the R-channel of the base image to update the R-channel of the base image. Similarly, if the acquired image is an LG image, the image processing section 17 allocates the LG image to the G-channel of the base image to update the G-channel of the base image. If the acquired image is an LB image, the image processing section 17 allocates the LB image to the B-channel of the base image to update the B-channel of the base image. Then, in step S204, the image processing section 17 performs the highlighting processing on the updated base image, based on an acquired highlighting amount, to generate a highlighted image.

If the acquired image is an LnB image (YES in step S201), the procedure goes to step S203, where the highlighting amount calculation section 17a of the image processing section 17 detects superficial blood vessels from the LnB image. The detection method is not specifically limited. For example, structure information may be detected by filter processing using a bandpass filter. In other words, the highlighting amount used in the highlighting processing in FIG. 6 corresponds to an output from the bandpass filter. Thereafter, in step S204, the highlighting processing section 17b highlights the base image using information about the superficial blood vessels detected in step S203. The highlighting method is not specifically limited. For example, the base image is highlighted by addition of the information about the detected superficial blood vessels to the G-channel of the base image. In this case, the highlighting processing performed by the highlighting processing section 17b is addition of the output from the bandpass filter to the base image.

As a result of the processing described in FIGS. 5 and 6, a corresponding channel of the base image is updated in the frame in which any one of the lights LB, LG, and LR is emitted. The base image is highlighted in the frame in which the light LnB is emitted. After the update of the given channel of the base image in step S202 or after the detection of the superficial blood vessels in step S203, the highlighted image is updated by the highlighting processing on the base image, based on the information about the detected superficial blood vessels. That is, in the example in FIG. 6, the highlighted image is updated in all the frames regardless of the acquired images. As mentioned above, it is the G-channel that helps the user to recognize the movement of the object easily. That is, from the user's view, the object $OB_G$ whose image is captured using the light LG moves in the frame in which the light LG is emitted, and the superficial blood vessels $OB_{nB}$ move in the frame in which the light LnB is emitted.

In the present embodiment, the order of emission is as illustrated in FIG. 3. Since the illumination section 3 emits the lights in the order of "LR, LG, LnB, and LB", the delay time of the movement of the superficial blood vessels from the movement of the other object corresponds to one frame. Accordingly, the present embodiment can improve image quality in comparison with the comparative example in FIG. 1.

Note that the specific order of emission may be subjected to various modifications. For example, only if the light LG is emitted immediately before the light LnB, a different order such as "LB, LG, LnB, and LR" is applicable. The method in accordance with the present embodiment only needs to reduce the time difference between the moving timing of the object $OB_G$ and the moving timing of the superficial blood vessels $OB_{nB}$, and the order of emitting the lights LG and LnB may be replaced with each other. For example, the lights may be in the order of "LR, LnB, LG, and LR". Also in this case, only if the light LnB is emitted immediately before the light LG, a different order such as "LB, LnB, LG, and LR" is applicable.

As the highlighting processing based on the LnB image, the method of adding the output from the bandpass filter to the G-channel has been described, but specific processing is not limited thereto. The highlighting amount calculation section 17a may determine the coefficient, as the highlighting amount, by referring to a lookup table based on the output from the bandpass filter. The lookup table may be stored in advance in the memory 16 or may be acquired from the outside using a network or the like. Alternatively, the highlighting amount calculation section 17a may perform division using the output from the bandpass filter and the LnB image, and determine the coefficient based on the result of the division. For example, the memory 16 stores a function for calculating the coefficient from the result of the division, and the highlighting amount calculation section 17a outputs the coefficient based on the function. While the bandpass filter is employed in the above description to detect the superficial blood vessels, various modifications can be made also in this respect. For example, known image processing for edge detection may be applied to detect the superficial blood vessels. Additionally, the highlighting processing section 17b may multiply the base image by the coefficient output from the highlighting amount calculation section 17a.

As described above, the image processing section 17 (the highlighting amount calculation section 17a) detects the specific structure, based on the second image (the LnB image) acquired by the emission of the second light (the light LnB). Further, the image processing section 17 (the highlighting processing section 17b) combines the information based on the detection result, with the first image (the LG image) acquired by the emission of the first light (the light LG), and thereby generates the highlighted image in which the specific structure is highlighted. The information based on the detection result may be a detection result itself such as the output from the bandpass filter, or may be information determined based on the detection result, i.e., the coefficient as exemplified above. The combining processing may be addition or multiplication. As far as the information based on the detection result is added to the LG image, the combining processing may be performed in a different manner. The present embodiment can thereby display the specific structure in a highly viewable manner to the user.

3. Second Embodiment

A second embodiment is described below. The configuration of the endoscope apparatus 1 is similar to that of the example described with reference to FIG. 2. The process flow is similar to the one illustrated in FIG. 5, except that the highlighted image generation processing described in step S103 is different from that of the first embodiment.

Figure 7:
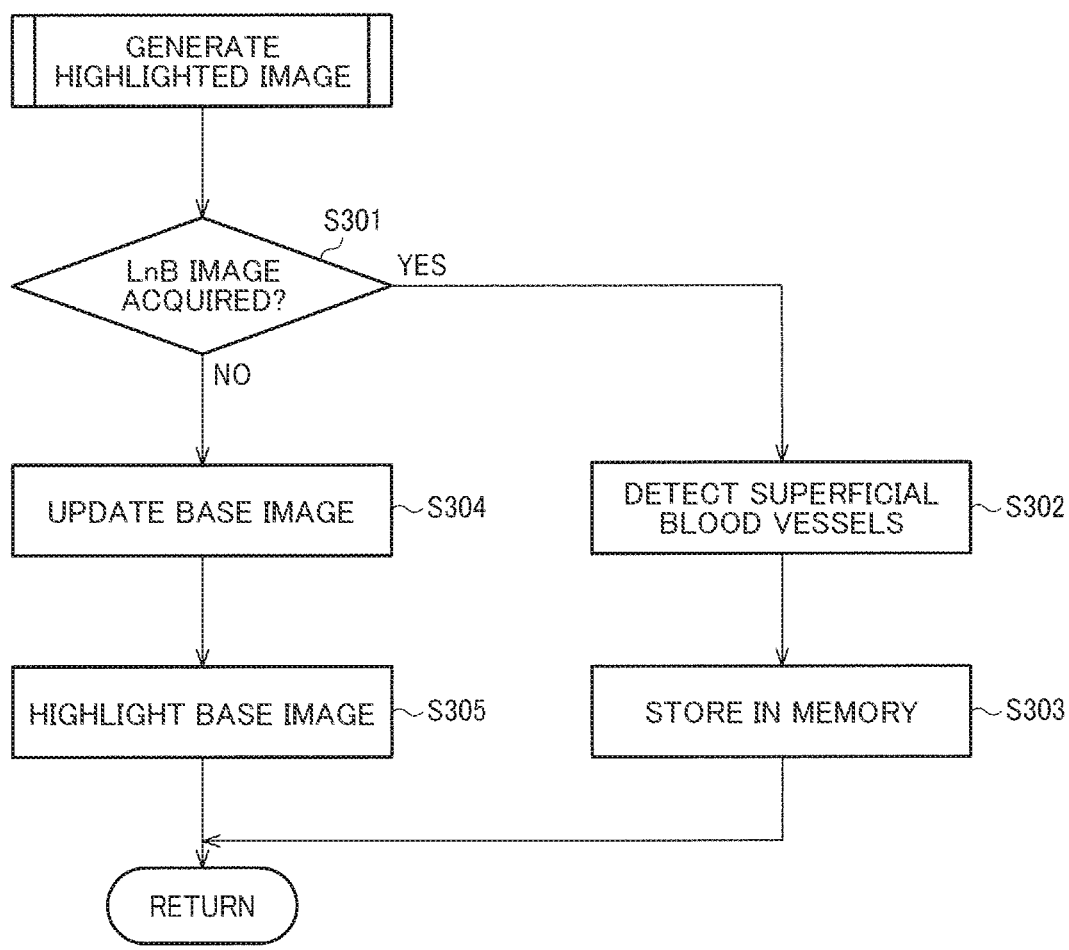
FIG. 7 is a flowchart describing highlighted image generation processing in accordance with the second embodiment.

FIG. 7 is a flowchart describing the highlighted image generation processing in accordance with the present embodiment. When this processing starts, the image processing section 17 first determines whether the image acquired in step S102 is an LnB image (step S301). If the acquired image is an LnB image (YES in step S301), the procedure goes to step S302, where the highlighting amount calculation section 17a of the image processing section 17 detects superficial blood vessels from the LnB image. Thereafter, in step S303, the highlighting amount calculation section 17a stores a result of the detection in the memory. The processing ends after step S303. That is, in the frame in which the LnB image is acquired, the present embodiment performs the processing up to the calculation of the highlighting amount, but performs neither the highlighting processing nor the update of the highlighted image.

If the acquired image is not an LnB image (NO in step S301), the procedure goes to step S304, where the image processing section 17 updates any one of the channels of the base image. Specifically, if the acquired image is an LR image, the image processing section 17 allocates the LR image to the R-channel of the base image to update the R-channel of the base image. Similarly, if the acquired image is an LG image, the image processing section 17 allocates the LG image to the G-channel of the base image to update the G-channel of the base image. If the acquired image is an LB image, the image processing section 17 allocates the LB image to the B-channel of the base image to update the B-channel of the base image.

After the processing in step S304, the highlighting processing section 17*b* performs the highlighting processing on the updated base image, based on information about the superficial blood vessels stored in the memory (step S305). The processing in step S305 is to highlight the G-channel of the base image, based on the highlighting amount stored in the memory by the processing in step S303.

As a result of the processing described in FIG. 7, a corresponding channel of the base image is updated in the frame in which either of the light LB or LR is emitted, and the highlighted image is also updated in this frame. The highlighting amount for the highlighting processing is calculated in the frame in which the light LnB is emitted. In the frame in which the light LG is emitted, the base image is updated, and the highlighted image is updated by the highlighting processing using the highlighting amount calculated at a past timing.

Figure 8:
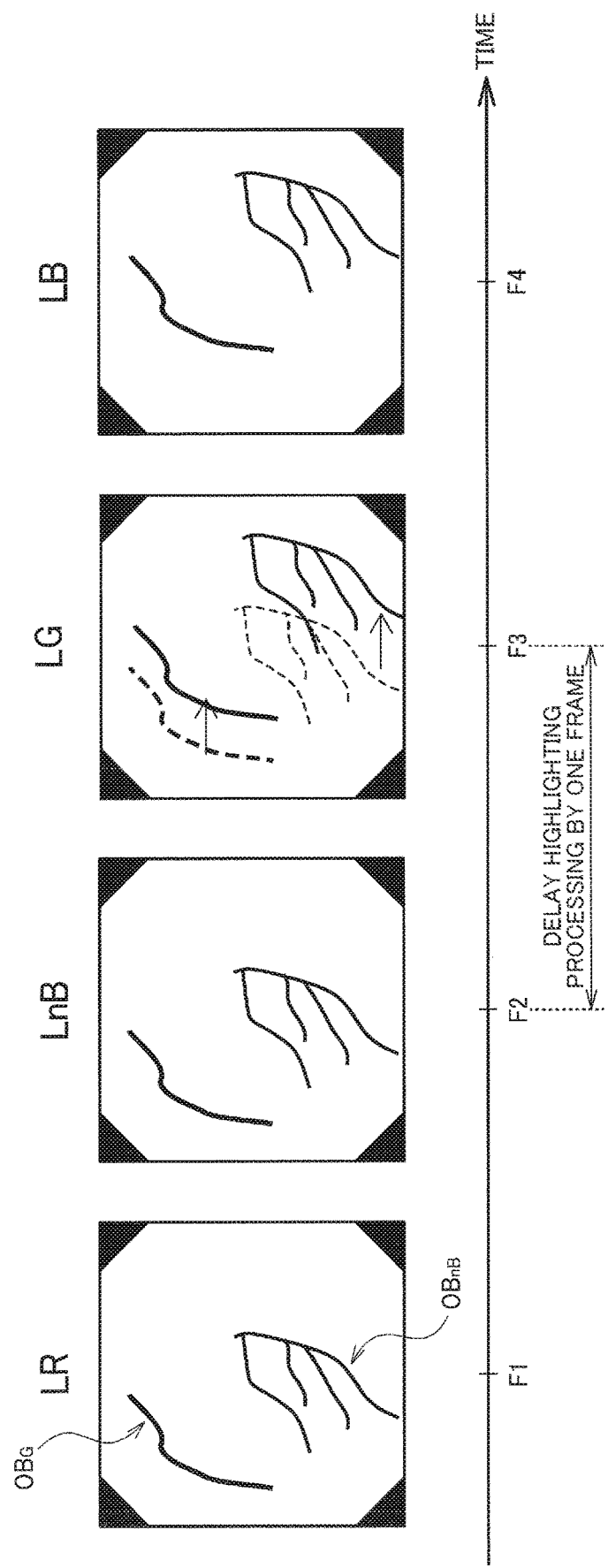
FIG. 8 illustrates the order of emitting illumination lights, and highlighted images, as an example in accordance with the second embodiment.

FIG. 8 illustrates the order of emitting illumination lights, and highlighted images, as an example in accordance with the present embodiment. In the present embodiment, the light LR is emitted in the frame F1, the light LnB is emitted in the frame F2, the light LG is emitted in the frame F3, and the light LB is emitted in the frame F4. This cycle is repeated in the subsequent frames, and the lights LR, LnB, LG, and LB are sequentially emitted in each period.

In the frame F1, the LR image is acquired by emission of the light LR. The base image in the R-channel is updated with this acquired image, and thereby the display image is updated. The frame F1 is similar to that of the first embodiment illustrated in FIG. 3.

In the frame F2, the LnB image is acquired by emission of the light LnB. Based on the LnB image, the highlighting amount is calculated, or, in a more limited sense, the superficial blood vessels are detected. At a timing of the frame F2, however, the present embodiment performs only the detection of the superficial blood vessels, and does not perform the highlighting processing. Eventually, unlike the example illustrated in FIG. 3, the highlighted image is not updated in the frame F2, and the movement of the superficial blood vessels OB$_{nB}$ does not occur in the frame F2, either.

In the frame F3, the LG image is acquired by emission of the light LG. The present embodiment generates a highlighted image in the frame in which the LG image is acquired, by performing both the update of the G-channel of the base image and the highlighting processing on the base image. Information to be used for the highlighting processing is information about the superficial blood vessels detected at the timing of the frame F2. Consequently, in the method of the present embodiment, the movement of the object OB$_G$ whose image is captured using the light LG occurs simultaneously with the movement of the superficial blood vessels OB$_{nB}$ in the frame F3.

In the frame F4, the LB image is acquired by emission of the light LB. The base image in the B-channel is updated with this acquired image, and thereby the display image is updated. The frame F4 is similar to that of the first embodiment illustrated in FIG. 3.

In the present embodiment, the illumination section 3 emits the second light (the light LnB) in the first frame, and emits the first light (the light LG) in the second frame following the first frame. In the example in FIG. 8, the first frame is the frame F2, and the second frame is the frame F3. In the first frame, the image processing section 17 acquires the second image (the LnB image) by the emission of the second light, and skips the processing of generating the highlighted image based on the second image. Then, in the second frame, the image processing section 17 generates the highlighted image by performing the highlighting processing on the first image (the LG image) acquired by the emission of the first light, based on the second image acquired in the first frame.

In this embodiment, "skipping the processing of generating the highlighted image" means, for example, that the superficial blood vessels are detected from the LnB image, but the information about the superficial blood vessels is not added to the base image. As a possible modification, the processing in the first frame is limited to the acquisition of the LnB image, and the processing of detecting the superficial blood vessels and the highlighting processing of adding the information about the superficial blood vessels to the base image are performed at the timing of the second frame.

The method in accordance with the present embodiment delays the timing of highlighting the superficial blood vessels until the frame corresponding to the emission of the light LG. Accordingly, in the highlighted display image, the movement of the superficial blood vessels occurs simultaneously with the movement of the object whose image is captured using the light LG. Since the movement of the superficial blood vessels is not delayed from the movement of the object whose image is captured using the light LG, it is possible to display an image with higher viewability and a reduced feeling of strangeness.

Note that the information about the superficial blood vessels to be used for the highlighting processing in the frame F3 is the information detected from the LnB image captured at the timing of the frame F2. Thus, the actual position of the superficial blood vessels at the timing of the frame F3 may possibly deviate from the displayed position of the superficial blood vessels on the highlighted image. However, by emitting the light LnB immediately before the emission of the light LG, the present embodiment can reduce the positional deviation between the displayed position and the actual position. Specifically, the positional deviation, which corresponds to the amount of movement in a period of one frame, is considered small enough to pose no problem on image display.

4. Third Embodiment

A third embodiment is described below. The configuration of the endoscope apparatus 1 is similar to that of the example described with reference to FIG. 2. The process flow is similar to the one illustrated in FIG. 5, except that the highlighted image generation processing described in step S103 is different from that of the first and second embodiments.

Figure 9:
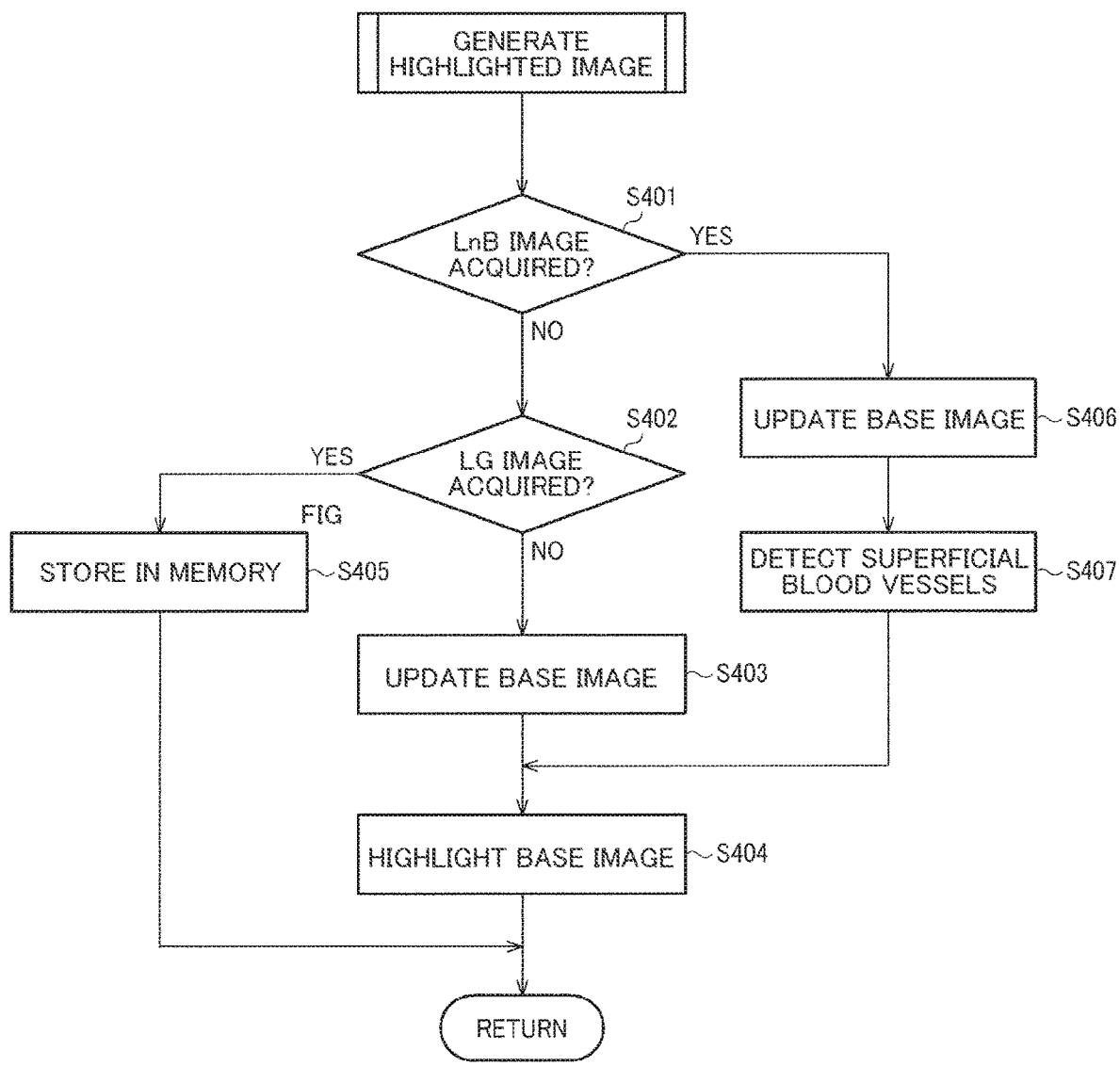
FIG. 9 is a flowchart describing highlighted image generation processing in accordance with the third embodiment.

FIG. 9 is a flowchart describing the highlighted image generation processing in accordance with the present embodiment. When this processing starts, the image processing section 17 first determines whether the image acquired in step S102 is an LnB image (step S401). If the acquired image is not an LnB image (NO in step S401), the procedure goes to step S402, where the image processing section 17 determines whether the acquired image is an LG image.

If the acquired image is an LR image or an LB image (NO in step S402), the procedure goes to step S403, where the image processing section 17 updates the base image. Specifically, if the acquired image is an LR image, the image processing section 17 allocates the LR image to the R-channel of the base image to update the R-channel of the base image. Similarly, if the acquired image is an LB image, the image processing section 17 allocates the LB image to the B-channel of the base image to update the B-channel of the base image. Further, in step S404, the highlighting processing section 17b performs the highlighting processing on the updated base image and thereby updates the highlighted image.

If the acquired image is an LG image (YES in step S402), the procedure goes to step S405, where the image processing section 17 stores the LG image in the memory 16 and then ends the processing. That is, in the frame in which the LG image is acquired, the present embodiment updates neither the base image nor the highlighted image.

If the acquired image is an LnB image (YES in step S401), the procedure goes to step S406, where the highlighting amount calculation section 17a of the image processing section 17 updates the base image with the LG image stored in the memory 16. Further, the image processing section 17 detects superficial blood vessels from the acquired LnB image (step S407), and then performs the highlighting processing on the base image, based on a result of the detection (step S404).

As a result of the processing described in FIG. 9, a corresponding channel of the base image is updated in the frame in which either of the light LB or LR is emitted, and thereby the highlighted image is also updated in this frame. In the frame in which the light LG is emitted, the processing is limited to the acquisition of the LG image, and neither the base image nor the highlighted image is updated. In the frame in which the LnB light is emitted, the highlighted image is updated by execution of both of the update of the base image with the LG image acquired in a past frame and the highlighting processing based on the LnB image.

Figure 10:
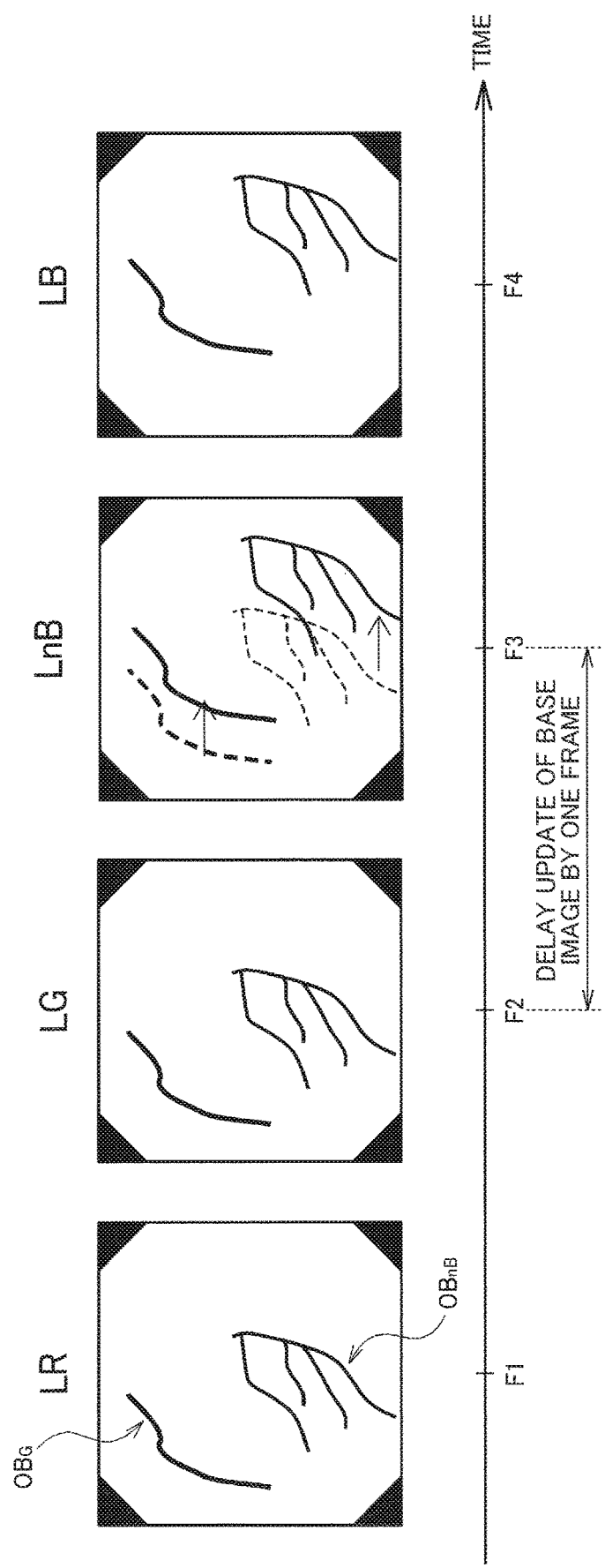
FIG. 10 illustrates the order of emitting illumination lights, and highlighted images, as an example in accordance with the third embodiment.

FIG. 10 illustrates the order of emitting illumination lights, and highlighted images, as an example in accordance with the present embodiment. In the present embodiment, the light LR is emitted in the frame F1, the light LG is emitted in the frame F2, the light LnB is emitted in the frame F3, and the light LB is emitted in the frame F4. This cycle is repeated in the subsequent frames, and the lights LR, LG, LnB, and LB are sequentially emitted in each period. Note that the order of emission is not limited thereto. Only if the light LnB is emitted immediately after the emission of the light LG, a different order such as "LB, LG, LnB, and LR" is applicable.

In the frame F1, the LR image is acquired by emission of the light LR. The base image in the R-channel is updated with this acquired image, and thereby the display image is updated. The frame F1 is similar to that of the first and second embodiments.

In the frame F2, the LG image is acquired by emission of the light LG. In the present embodiment, the acquired LG image is simply stored in the memory 16. Eventually, unlike the example illustrated in FIG. 3, the highlighted image is not updated at the timing of the frame F2, and the movement of the object $OB_G$ whose image is captured using the light LG does not occur at this timing, either.

In the frame F3, the LnB image is acquired by emission of the light LnB. In the present embodiment, the base image is updated in the frame F3 with the LG image acquired and stored at the timing of the frame F2. The highlighting processing on the base image is also performed in the frame F3, based on the LnB image. Consequently, in the method according to the present embodiment, the movement of the object $OB_G$ whose image is captured using the light LG occurs simultaneously with the movement of the superficial blood vessels $OB_{nB}$ in the frame F3.

In the frame F4, the LB image is acquired by emission of the light LB. The base image in the B-channel is updated with this acquired image, and thereby the display image is updated. The frame F4 is similar to that of the first and second embodiments.

In the present embodiment, the illumination section 3 emits the first light (the light LG) in the first frame, and emits the second light (the light LnB) in the second frame following the first frame. In the example in FIG. 10, the first frame is the frame F2, and the second frame is the frame F3. In the first frame, the image processing section 17 acquires the first image (the LG image) by the emission of the first light, and skips the processing of generating the highlighted image based on the first image. Then, in the second frame, the image processing section 17 generates the highlighted image by performing the highlighting processing on the first image acquired in the first frame, based on the second image (the LnB image) acquired by the emission of the second light.

In this embodiment, "skipping the processing of generating the highlighted image" means that the acquired LG image is not allocated to the base image, i.e., not allocated to any one of the output channels.

The method in accordance with the present embodiment delays the timing of updating the G-channel corresponding to the luminance component of the output until the timing of highlighting the superficial blood vessels. Accordingly, in the highlighted display image, the movement of the superficial blood vessels occurs simultaneously with the movement of the object whose image is captured using the light LG. Since the movement of the superficial blood vessels is not delayed from the movement of the object whose image is captured using the light LG, it is possible to display an image with higher viewability and a reduced feeling of strangeness.

Note that the LG image to be used for updating the base image at the timing of the frame F3 is the image captured in the frame F2. Thus, as for the object whose image is captured using the light LG, the actual position of the object at the timing of the frame F3 may possibly deviate from the displayed position of the object on the highlighted image. However, by emitting the light LG immediately before the emission of the light LnB, the present embodiment can sufficiently reduce the positional deviation.

As described by the second and third embodiments, the image processing section 17 of the endoscope apparatus 1 performs different types of image processing depending on the order of emission of the first light and the second light. When the first light is emitted earlier, the image processing section 17 performs the processing in FIG. 9 as described in the third embodiment. When the second light is emitted earlier, the image processing section 17 performs the processing in FIG. 7 as described in the second embodiment. This enables appropriate image processing in accordance with the order of emission, thereby enabling generation of the highlighted image having less degraded image quality.

5. Modification

Some modifications are described below.

In the foregoing description, the plurality of illumination lights with the different wavelength bands is composed of four lights LB, LG, LR, and LnB. Note that the plurality of illumination lights in accordance with the present embodiments only needs to include the first light corresponding to the luminance component of the output, and the second light enabling capturing of the image of the specific structure with higher contrast. Specific combinations of the illumination lights can be modified in various manners.

For example, it is possible to add a narrow-band light LnR corresponding to the red wavelength band and/or to add a narrow-band light LnG corresponding to the green wavelength band. The number of narrow-band lights corresponding to each color is not limited to one. For example, it is possible to add two narrow-band lights LnG1 and LnG2 corresponding to the green wavelength band.

Alternatively, part or all of the lights LB, LG, and LR can be omitted. For example, the illumination section 3 emits the lights LG, LR, and LnB. The image processing section 17 allocates the LnB image to the B-channel of the base image, and also uses the LnB image for the highlighting processing on the G-channel of the base image.

Each of the above-described examples allows, in each frame, one LED to emit light and one illumination light to be emitted to the object. However, emission control is not limited thereto, and a plurality of illumination lights may be emitted in each frame. For example, the lights LB and LnB are emitted together in the frame F4 in FIG. 3. The image captured by combined emission of the lights LB and LnB is brighter with higher viewability than the image captured by single emission of the light LB. Then, the image captured by the combined emission of the lights LB and LnB is allocated to the B-channel of the base image to improve viewability of the highlighted image. However, it is not easy to extract a component corresponding to the LnB image singly from the image captured by the combined emission of the lights LB and LnB. Accordingly, in this case, it is desirable to perform emission of the lights LB+LnB for acquiring the base image and emission of the light LnB for the highlighting processing in different frames. For example, where one period is composed of four frames, the illumination section 3 emits the lights in the order of "LR, LG, LnB, and LB+LnB".

The number of "the plurality of lights with the different wavelength bands" may, but does not have to, match the number of times of emitting the lights (the number of frames) in one period. This is because the illumination section 3 may emit a plurality of lights in one frame, or emit the same light more than once in one period. In the present embodiment, the number of frames per period simply needs to be two or greater. Note that, as the number of frames in one period increases, it is highly probable that the interval between the emission of the first light (the light LG) and the emission of the second light (the light LnB) is greater, which may make the delayed movement conspicuous. Thus, the method according to the present embodiment produces a significant effect especially when one period includes many frames. The number of frames per period is three or greater in a limited sense, and four or greater in a more limited sense.

Regarding the illumination section 3, FIG. 2 illustrates the example of providing a plurality of light sources respectively emitting the lights LR, LG, LB, and LnB. However, the configuration of the illumination section 3 is not limited thereto. For example, the illumination section 3 includes a white light source and a rotating filter. The white light source emits a white light having an even intensity for each wavelength in a visible range. The white light source is, for example, an LED or a xenon lamp. The rotating filter includes a plurality of color filters with different transmission wavelength bands. The rotating filter transmits the white light while rotating, and thereby sequentially emits lights with different wavelength bands to the guide cable 8.

In the example of emitting the four lights LR, LG, LB, and LnB, the rotating filter includes four color filters with different transmission wavelength bands for the respective lights.

The description has been given on the assumption that the image sensor 12 is a monochrome filter without a color filter. Instead, the image sensor 12 may be a sensor having a color filter. The color filter may be a color filter in a well-known Bayer's arrangement, a complementary color filter, or a color filter in another arrangement.

As the types of endoscope apparatus, the present disclosure may assume a type in which a scope is connected to a control device and operated by a user to capture an image of the inside of the living body. However, the present disclosure is not limited to this type of endoscope apparatus, and is also assumed to be applicable, for example, to an endoscope apparatus in a surgery support system using a robot.

Such a surgery support system includes, for example, a control device, a robot, and a scope. The scope is, for example, a rigid scope. The control device is a device that controls the robot. That is, the user operates an operation section of the control device to move the robot, and performs surgery on a patient through the robot. In addition, the user operates the operation section of the control device to manipulate the scope through the robot and capture images of a surgical region. The control device includes the processing section 4 illustrated in FIG. 2. The user operates the robot while watching images displayed on a display device by the processing section 4. The present embodiments can be applied to the control device in such a surgery support system. The control device may be integrated in the robot.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
a light source configured to emit a plurality of lights with different wavelength bands with at least two different timings in time series, the plurality of lights comprising a first light and a second light; and
a processor comprising hardware,
wherein the processor is configured to generate a highlighted image in which a specific structure under a mucus membrane is highlighted, based on a plurality of images obtained by the emission of the plurality of lights,
wherein the light source is configured to emit the first light and the second light, the first light having a first wavelength band corresponding to a luminance component of the highlighted image, and the second light having a second wavelength band that enables capturing of an image of the specific structure with higher contrast than the first light, wherein the processor is configured to:
when an image acquired at a first timing in a cycle of emitting the plurality of lights is a second light image captured by emission of the second light and an image acquired at a second timing after the first timing in the cycle is a first light image captured by emission of the first light,
skip a process of adding information about the specific structure detected from second light image to an image for display for a frame corresponding to the first timing; and
generate the highlighted image for display for a frame corresponding to the second timing based on the first light image captured by emission of the first light and the information about the specific structure detected from the second light image; and
when the image acquired at the first timing in the cycle is the first light image captured by emission of the first light and the image acquired at the second timing after the first timing in the cycle is the second light image captured by emission of the second light,
skip a process of generating the image for display for the frame corresponding to the first timing based on the first light image; and
generate the highlighted image for display for the frame corresponding to the second timing based on the first light image captured by emission of the first light and the information about the specific structure detected from the second light image.

2. The endoscope apparatus as defined in claim 1, wherein the plurality of lights with the different wavelength bands includes light in a red wavelength band, light in a green wavelength band and light in a blue wavelength band.

3. The endoscope apparatus as defined in claim 1, wherein the specific structure corresponds to blood vessels.

4. An operating method of an endoscope apparatus, the operating method comprising:
emitting a plurality of lights with different wavelength bands with at least two different timings in time series, the plurality of lights comprising a first light and a second light; and
generating a highlighted image in which a specific structure under a mucus membrane is highlighted, based on a plurality of images obtained by the emission of the plurality of lights,
wherein the emission of the plurality of lights includes emitting the first light and the second light, the first light having a first wavelength band corresponding to a luminance component of the highlighted image, and the second light having a second wavelength band that enables capturing of an image of the specific structure with higher contrast than the first light,
wherein, when an image acquired at a first timing in a cycle of emitting the plurality of lights is a second light image captured by emission of the second light and an image acquired at a second timing after the first timing in the cycle is a first light image captured by emission of the first light:
skipping a process of adding information about the specific structure detected from a second light image to an image for display for a frame corresponding to the first timing; and
generating the highlighted image for display for a frame corresponding to the second timing based on the first light image captured by emission of the first light and the information about the specific structure detected from the second light image, and wherein, when the image acquired at the first timing in the cycle is the first light image captured by emission of the first light and the image acquired at the second timing after the first timing in the cycle is the second light image captured by emission of the second light:
skipping a process of generating the image for display for the frame corresponding to the first timing based on the first light image; and
generating the highlighted image for display for the frame corresponding to the second timing based on the first light image captured by emission of the first light and the information about the specific structure detected from the second light image.

5. A non-transitory information storage medium storing a program, the program causing a computer to at least perform:
causing a light source to emit a plurality of lights with different wavelength bands with at least two different timings in time series, the plurality of lights comprising a first light and a second light; and
generating a highlighted image in which a specific structure under a mucus membrane is highlighted, based on a plurality of images obtained by the emission of the plurality of lights,
wherein emitting the plurality of lights includes emitting the first light and the second light, the first light having a first wavelength band corresponding to a luminance component of the highlighted image, and the second light having a second wavelength band that enables capturing of an image of the specific structure with higher contrast than the first light,
wherein, when an image acquired at a first timing in a cycle of emitting the plurality of lights is a second light image captured by emission of the second light and an image acquired at a second timing after the first timing in the cycle is a first light image captured by emission of the first light:
skipping a process of adding information about the specific structure detected from a second light image to an image for display for a frame corresponding to the first timing; and
generating the highlighted image for display for a frame corresponding to the second timing based on the first light image captured by emission of the first light and the information about the specific structure detected from the second light image, and
wherein, when the image acquired at the first timing in the cycle is the first light image captured by emission of the first light and the image acquired at the second timing after the first timing in the cycle is the second light image captured by emission of the second light:
skipping a process of generating the image for display for the frame corresponding to the first timing based on the first light image; and
generating the highlighted image for display for the frame corresponding to the second timing based on the first light image captured by emission of the first light and the information about the specific structure detected from the second light image.

* * * * *